United States Patent
Barthelemy et al.

(10) Patent No.: US 9,050,268 B2
(45) Date of Patent: Jun. 9, 2015

(54) FUNCTIONAL AMPHIPILIC MOLECULE OR MACROMOLECULE FORMULATIONS WITH MULTIPLE COMPARTMENTS

(75) Inventors: Philippe Barthelemy, Merignac (FR); Salim Khiati, Bordeaux (FR); Michel Camplo, Marseille (FR)

(73) Assignees: UNIVERSITE d'AIX-MARSEILLE, Marseilles (FR); UNIVERSITE DE BORDEAUX, Bordeaux (FR)

( * ) Notice: Subject to any disclaimer, the term of this patent is extended or adjusted under 35 U.S.C. 154(b) by 20 days.

(21) Appl. No.: 13/322,986

(22) PCT Filed: May 28, 2010

(86) PCT No.: PCT/FR2010/000401
§ 371 (c)(1),
(2), (4) Date: Nov. 29, 2011

(87) PCT Pub. No.: WO2010/136676
PCT Pub. Date: Dec. 2, 2010

(65) Prior Publication Data
US 2012/0070505 A1    Mar. 22, 2012

(30) Foreign Application Priority Data

May 29, 2009  (FR) ...................................... 09 02607

(51) Int. Cl.
*A61K 9/16* (2006.01)
*A61K 9/51* (2006.01)
(52) U.S. Cl.
CPC ........................................ *A61K 9/51* (2013.01)

(58) Field of Classification Search
None
See application file for complete search history.

(56) References Cited

U.S. PATENT DOCUMENTS

| | | | |
|---|---|---|---|
| 6,001,817 A | 12/1999 | Shaw | |
| 7,908,160 B2 | 3/2011 | Bhargava | |
| 2003/0219384 A1 | 11/2003 | Donath et al. | |
| 2004/0247660 A1* | 12/2004 | Singh | 424/450 |
| 2008/0089836 A1 | 4/2008 | Hainfeld | |

FOREIGN PATENT DOCUMENTS

| | | |
|---|---|---|
| WO | WO 0132139 A2 | 5/2001 |
| WO | WO 2005116043 A1 * | 12/2005 |

OTHER PUBLICATIONS

Jain et al., "Effect of the structure of phospholipid on the kinetics of intravesicle scooting of phospholipase A2", Biochim Biophys Acta Biomembranes 860:462 (1986).*

* cited by examiner

*Primary Examiner* — Sue Liu
*Assistant Examiner* — Thor Nielsen
(74) *Attorney, Agent, or Firm* — Browdy and Neimark, PLLC

(57) ABSTRACT

The invention relates to novel functional amphiphilic molecule or macromolecule formulations with multiple compartments for transporting or targeting at least one therapeutic agent, in particular an antitumor agent, as well as to a method for preparing such formulations and to the use thereof.

19 Claims, 7 Drawing Sheets

NP1

NP2

NP3

7A

7B

7C

7D

US 9,050,268 B2

FUNCTIONAL AMPHIPILIC MOLECULE OR MACROMOLECULE FORMULATIONS WITH MULTIPLE COMPARTMENTS

The invention relates to novel functional amphiphilic molecule or macromolecule formulations with multiple compartments for the transporting or targeting of at least one therapeutic agent, in particular an anti-neoplastic agent as well as a method for preparing such formulations, and to the use thereof.

Among the anti-neoplastic agents, cisplatin is an anti-neoplastic agent which is widely used, in particular for the treatment of solid tumors. However, its use is limited by its toxicity as well as the occurrence of an acquired resistance.

In order to remedy these drawbacks, different formulations have been proposed in the prior art: for example, U.S. Pat. No. 5,178,876 describes platinum derivatives in the form of hydrophobic complexes intended for encapsulation in liposomes.

U.S. Pat. No. 6,001,817 describes compositions containing cisplatin and a carrier comprising at least one nucleoside or deoxynucleoside.

U.S. Pat. No. 7,908,160 relates to cisplatin derivatives bound to ligands, the activity of which is reversible depending on the bond to the ligand.

Patent application WO01/32139 describes cisplatin compositions encapsulated in lipid nanoparticles obtained by repeated freezing and thawing cycles, based on negatively charged natural lipids, in particular dioleylphosphatidylserine. It is indicated in this application that cisplatin forms, in water, positively charged aggregates having a higher solubility than the non-charged species, which allows their interaction with the negatively charged lipid membranes and the reorganization of the lipid membranes around the cisplatin aggregates.

However, a need also exists to resolve the problems linked to the targeting of therapeutic agents, in particular the anti-neoplastic agents.

In particular, a means is sought to allow the therapeutic agents (in particular cisplatin and/or its derivatives) to be transported rapidly to the interior of tumor cells with a high pharmacological activity whilst preserving healthy cells, i.e. by reducing the neurological, renal, auditory, digestive toxicity, etc., by simultaneously limiting the phenomena of the appearance of resistance to this therapeutic agent.

It is also sought to provide a carrier having a sufficient stability over time to avoid the early release of the therapeutic agent and the drawbacks associated with the presence of the free therapeutic agent in the biological medium, in particular in terms of loss of activity and toxicity.

Moreover, the possibility of encapsulating one or more therapeutic agents in the same formulation in different compartments of the same formulation has the benefit of allowing a simultaneous or staggered delivery of this (these) agent(s) to the same target, each of the compartments being able to serve as a reservoir.

It has now been found that formulations with multiple compartments, formed from functional amphiphilic molecules or macromolecules, exhibited improved stability properties, in particular at 37° C., allowing a sustained targeting of said therapeutic agents over time and allowing the efficient and rapid intracellular delivery of therapeutic agents.

A subject of the invention is therefore, according to a first aspect, a formulation with multiple compartments in the form of nanoparticles constituted by a solid core containing a therapeutic agent, surrounded by at least two lipid layers of different polarity formed from functional amphiphilic molecules or macromolecules.

BRIEF DESCRIPTION OF DRAWINGS

FIG. 3A) and SKV03 cells (cisplatin-resistant ovarian adenocarcinoma line; FIG. 3B) treated with free cisplatin or cisplatin encapsulated in the nanoparticles of Example 10, which corresponds to the concentration of cisplatin internalized in the treated cells.

Figure 1:
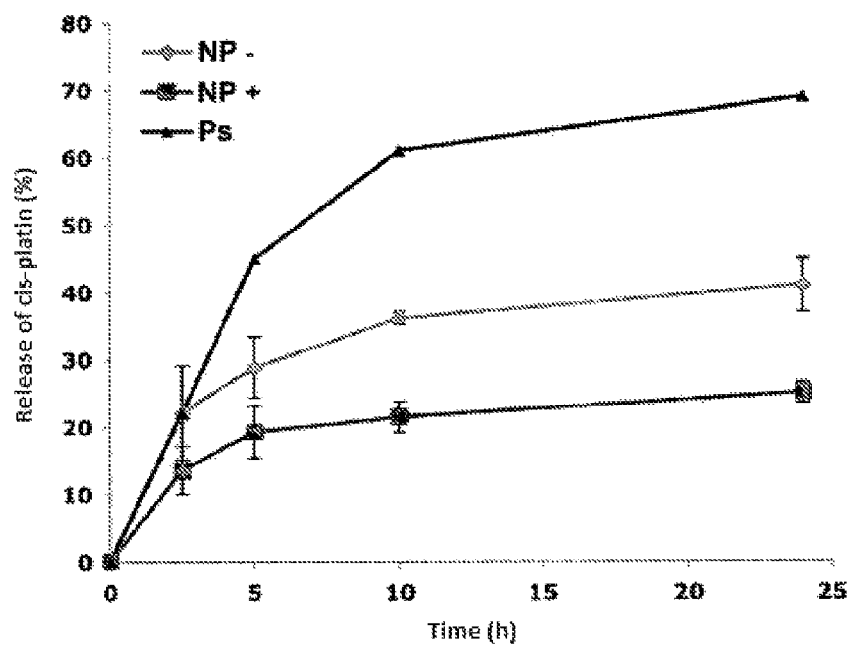
FIG. 1 represents the curve of the release of cisplatin from the nanoparticles as a function of the incubation time (ICP optical spectrometry), where the nanoparticles prepared according to the protocol of example 10 or from the nanoparticles based on 1,2-dioleoyl-sn-glycero-3-[phospho-L-serine] (DOPS) with 1-2-dioleoyl-sn-glycero-3-phosphocholine (DOPC) as a co-lipid as a comparison (single anionic lipid layer).

By "nanoparticle", is meant a particle having an average diameter of approximately 1 to 200 nm, preferably of 25 to 150 nm.

In the remainder of the description, by "nanoparticle according to the invention" or "nanoparticle with multiple compartments" is meant a formulation with multiple compartments in the form of nanoparticles constituted by a solid core containing a therapeutic agent, surrounded by at least two lipid layers of different polarity formed from functional amphiphilic molecules or macromolecules.

Advantageously, each lipid layer constitutes a compartment which can comprise a therapeutic agent identical to or different from that present in the core.

According to an advantageous aspect, the formulations with multiple compartments according to the invention are formed from said lipid layers of different polarity in the presence of the therapeutic agent(s) and not from a preformed particle, which allows a "customized" encapsulation of the active ingredient in the desired compartment(s), depending on the desired activity.

This particular structure confers upon the nanoparticles with multiple compartments according to the invention a stability (life span) compatible with the delivery of a therapeutic agent, and allows their disintegration after the release of this therapeutic agent.

Preferably, the first lipid layer is constituted by one or more anionic lipid(s) and the second lipid layer is constituted by one or more cationic lipid(s).

By "of different polarity", is meant that each successive lipid layer surrounding the core is constituted by lipids different from the previous one and that each layer has an overall surface charge which is either negative (constituted by anionic lipids) or positive (constituted by cationic lipids), or neutral (constituted by neutral lipids). For example, a first lipid layer can be formed by anionic lipids and will carry a negative surface charge, whereas the second lipid layer can be formed by cationic lipids and will carry a positive surface charge.

The surface charge of each of the layers can be measured by their zeta potential, for example, according to the technique described in Andrea Mayer et al. Toxicology, 2009, 258, 139-147 or K. Furusawa and K. Uchiyama, 1988, 140, 217-226.

According to an advantageous aspect, the nanoparticles with multiple compartments according to the invention can comprise alternating anionic and cationic lipid layers and an external layer constituted by one or more neutral lipid(s).

According to a preferred aspect, each lipid layer is constituted by at least one functional amphiphilic compound of formula (I)
in which

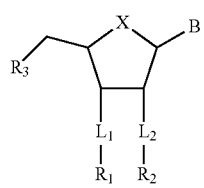
(I)

X represents an oxygen or sulphur atom or a methylene group,
B represents a purine or pyrimidine base such as uracil, adenine, guanine, cytosine, thymine, hypoxanthine, or their derivatives, or also an non-natural mono- or bicyclic heterocylic base each ring of which comprises 4 to 7 members, optionally substituted;
$L_1$ and $L_2$, identical or different, represent hydrogen, an oxycarbonyl —O—C(O)— group, a thiocarbamate —O—C(S)—NH— group, a carbonate —O—C(O)—O— group, a carbamate —O—C(O)—NH— group, an oxygen atom, a phosphate group, a phosphonate group or a heteroaryl group comprising 1 to 4 nitrogen atoms, unsubstituted or substituted by a linear or branched, saturated or unsaturated $C_2$-$C_{30}$ hydrocarbon chain, or also, $L_1$ and $L_2$, together, form a ketal group of formula

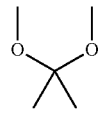

or also $L_1$ or $L_2$ represents hydrogen, and the other represents a hydroxy group or a heteroaryl group comprising 1 to 4 nitrogen atoms, unsubstituted or substituted by a linear or branched $C_2$-$C_{30}$ alkyl chain;
$R_1$ and $R_2$, identical or different, represent
a linear or branched $C_2$-$C_{30}$ hydrocarbon chain, preferably $C_6$-$C_{25}$, in particular $C_8$-$C_{25}$, saturated or partially unsaturated, optionally completely or partially fluorinated, unsubstituted or substituted on the carbon at the end of the chain by a fluorine atom or by a benzyl or naphthyl ester or ether, or
a diacyl chain in which each acyl chain is $C_2$-$C_{30}$, or
a diacylglycerol, sphingosine or ceramide group, or
when $L_1$ or $L_2$ represents hydrogen, and the other represents a hydroxy group or a heteroaryl group comprising 1 to 4 nitrogen atoms, $R_1$ and $R_2$ do not exist;
$R_3$ represents:
a hydroxy, amino, phosphate, phosphonate, phosphatidylcholine, O-alkyl phosphatidylcholine, thiophosphate, phosphonium, $NH_2$—$R_4$, $NHR_4R_5$ or $NR_4R_5R_6$ group in which $R_4$, $R_5$ and $R_6$, identical or different, represent a hydrogen atom or a linear or branched $C_1$-$C_5$ alkyl or linear or branched $C_1$-$C_5$ hydroxyalkyl chain, or
a linear or branched $C_2$-$C_{30}$ alkyl chain optionally substituted by a hydroxy group, or
a cyclodextrin radical, or
a

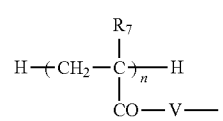

radical in which V represents an —O—, —S—, or —NH— bond, $R_7$ represents H or $CH_3$, and n=1 to 500, or
a —$(CH_2)_n$—V—$R_8$ group, in which $R_8$ represents a $C_2$-$C_{30}$ alkyl, and n=1 to 500, or
a heteroaryl group containing 1 to 4 nitrogen atoms, unsubstituted or substituted by a $C_2$-$C_{30}$ alkyl, or by a $(CH_2)_m$—O—$(CH_2)_p$—$R_9$ group in which m=1 to 6 and p=0 to 10 and $R_9$ represents a cyclic ketal group containing 5 to 7 carbon atoms, unsubstituted or substituted by at least one linear or branched $C_2$-$C_{30}$ alkyl or by a sterol radical, or also
$R_3$ is linked by a covalent bond to another substituent $R_3$, identical or different, of another compound of formula (I), identical or different, in order to form a compound of formula (I) in the form of a dimer,
and each lipid layer has a polarity different from that of the previous one.

The charge of the compounds of formula (I) is determined by the polar groups that they contain, these being essentially present in or constituted by the substituents $L_1$, $L_2$ and/or $R_3$.

Anionic compounds of formula (I) which can be used for preparing the first lipid layer can be, for example, chosen from anionic nucleolipids such as compounds of formula (I) in which $L_1$, $L_2$ and/or $R_3$ represent a negatively charged group such as, for example, a phosphate, phosphonate, carboxylate, sulphate group, etc., optionally substituted.

Cationic compounds of formula (I) which can be used for preparing the first lipid layer can be, for example, chosen from the cationic nucleolipids such as compounds of formula (I) in which $L_1$, $L_2$ and/or $R_3$ represent a positively charged group such as, for example an ammonium, phosphonium, imidazolium group, etc., optionally substituted.

The charge of these polar groups can also vary depending on the pKa of these groups, for example when it is an amine, imidazole, phosphate group, etc.

By "therapeutic agent", is meant, for example, a natural or synthetic molecule used for the prevention or treatment of a pathology or the restoration of a biological function, in vitro or in vivo, in particular in animals, including humans, or also on isolated cells, with the exception of the nucleic acids or their fragments.

Such a molecule can be chosen, for example, from the active ingredients of medicaments, in particular from the anti-neoplastic agents such as, for example:
  the platinum complexes, among which there can in particular be mentioned cisplatin, carboplatin, oxaliplatin, nedaplatin, lobaplatin, etc., or
  ruthenium which can bind to platinum complexes, or also inorganic complexes without platinum based on ruthenium II and/or III, titanium, for example titanocene dichloride, or gallium, for example the gallium salts such as gallium nitrate, gallium chloride, KP46, or
  iron derivatives, such as, for example, ferrocenium salts, nucleoside analogues containing iron, iron (II) complexes containing pyridyl-pentadentate ligands, or
  cobalt derivatives, such as, for example, hexacarbonyldicobalt complexes, alkyne-cobalt complexes, Co(III) complex containing a nitrogen mustard ligand, or
  gold derivatives such as, for example, Auranofin, gold (I), (III) and (III) complexes, aurothioglucose, etc.

Advantageously, the formulation with multiple compartments according to the invention makes it possible to encapsulate these molecules and ensure their intracellular delivery while limiting the phenomena of acquired resistance to these compounds.

The platinum complexes, in particular cisplatin, are preferred therapeutic agents for the purposes of the invention.

Inorganic complexes based on ruthenium II and/or III, can be, for example, the complexes called NAMI-A, RAPTA-C, KP1019. Such non-platinum complexes are described in Ott I. and Gust R., *Arch. Pharm. Chem. Life Sci.* 2007, 340, 117-126; Reedijk J., Curr Opin Chem Biol., 1999, 3, 236-40; Haimei Chen et al., J. Am. Chem. Soc, 2003, 125, 173-186.

Nucleoside analogues containing iron are described in Schlawe D. et al., Angew. Chem. Int. Ed., 2004, 1731-1734.

Advantageously, it has been found that the molecular and/or macromolecular structures which constitute the compounds of formula (I), comprising at least one ligand of the therapeutic agent (nucleobase, nucleoside, modified nucleoside, nucleotides, oligonucleotide, heterocycle, etc) represented by the substituent B, and having an amphiphilic character due to the presence of at least one hydrophilic part (phosphate, carboxylate, etc), and of at least one hydrophobic part (hydrophobic segments which are single-stranded, double-stranded and polar parts derived from synthons of biological origin, etc.), made it possible to form stable nanoparticles with the therapeutic agent.

By combining the amphiphilic properties of the compounds of formula (I), the presence of ligands of the therapeutic agent (active ingredient) in these compounds and any electrostatic interactions between the therapeutic agents and these compounds, the nanoparticles thus obtained have a structure which allows an effective and rapid intracellular delivery of the encapsulated active ingredients, in particular anti-neoplastic agents.

Without wishing to restrict the invention to one theory, it can be postulated that the intermolecular interactions of the compounds of formula (I) lead to an increase in the cohesion forces on the surface of the nanoparticles, which results in a greater stability over time, under the conditions of use.

The structure with multiple compartments of the nanoparticles according to the invention, based on multiple lipid layers having an adjustable polarity, confers upon them numerous advantages, in particular:
  an increased stability, in particular in biological medium,
  the adjustment of the surface potential (zeta potential) depending on their effectiveness in the envisaged use,
  their functionalization (introduction of a functionality, targeting agent, etc),
  the incorporation of different therapeutic agents.

Advantageously, said nanoparticles also have a life span compatible with their use as a carrier for a therapeutic agent.

In formula (I) above, n is advantageously comprised between 1 and 500, preferably comprised between 1 and 100, in particular comprised between 1 and 50, quite particularly comprised between 1 and 10.

By "linear or branched $C_1$-$C_5$ alkyl", is meant for example a methyl, ethyl, propyl, i-propyl, n-butyl, i-butyl, tert-butyl radical, preferably methyl or ethyl.

Also, in formula (I) above, the purine or pyrimidine base, or the non-natural heterocyclic base can be substituted by at least one substituent chosen, for example, from a halogen, an amino group, a carboxy group, a carbonyl group, a carbonylamino group, a hydroxy, azido, cyano, alkyl, cycloalkyl, perfluoroalkyl, alkyloxy (for example, methoxy), oxycarbonyl, vinyl, ethynyl, propynyl, acyl group etc.

By "non-natural heterocyclic base" is meant a base other than uracile, adenine, guanine, cytosine, thymine or hypoxanthine, which does not exist in nature.

By "heteroaryl group containing 1 to 4 nitrogen atoms", is meant a monocyclic or bicyclic, aromatic or partially unsaturated, carbocyclic group containing 5 to 12 atoms, interrupted by 1 to 4 nitrogen atoms, in particular the pyrazole, triazole, tetrazole or imidazole groups.

For the preparation of the compounds of formula (I), reference can be made to the application WO 2005/116043, which describes different access routes to this type of compounds (see in particular pp. 8-17 and examples).

According to a subsequent aspect, the invention also relates to a method for preparing a formulation with multiple compartments in the form of solid nanoparticles constituted by a core containing a therapeutic agent, surrounded by at least two lipid layers of different polarity formed from functional amphiphilic molecules or macromolecules, in which each lipid layer constitutes a compartment which can comprise a therapeutic agent identical to or different from that present in the core, comprising the following steps:
  a) preparing a mixture of at least one functional amphiphilic molecule or macromolecule, in particular a functional amphiphilic compound of formula (I) as defined above, and a therapeutic agent, b) subjecting said mixture to repeated heating and freezing cycles, in order to obtain nanoparticles containing said therapeutic agent, and c) recovering the nanoparticles containing said therapeutic agent thus obtained, d) bringing said nanoparticles into the presence of at least one functional amphiphilic molecule or macromolecule, in particular a functional amphiphilic compound of formula (I) as defined above, having a polarity different from that utilized in step a), and e) recovering the multi-compartment nanoparticles thus obtained.

Preferably, the therapeutic agent is an anti-neoplastic agent, in particular a platinum complex, in particular cisplatin.

Advantageously, the steps of the method can be repeated the number of times necessary to obtain the desired number of lipid layers.

Optionally, an additional step consisting of the formation of a neutral lipid layer constituted by at least one functional amphiphilic molecule or macromolecule, in particular a functional amphiphilic compound of formula (I) as defined above, said molecule or said compound of formula (I) being neutral, can be carried out between step d) and step e).

According to a preferred aspect, in step a) and/or step d), at least one co-lipid will be used in addition to the functional amphiphilic compound.

By "co-lipid", is meant a compound used in combination with the compound of formula (I), which contributes to the production of the structure of the lipid layers(s) of the nanoparticle.

Preferably, a zwitterionic co-lipid will be used.

Said co-lipid can be, for example, chosen from dioleylphosphatidylcholine (DOPC), dioleylphosphatiduridine-phosphatidylcholine (DOU PC) or dioleylphosphatidylethanolamine (DOPE).

These compounds can play the role of co-lipid when they are used in a mixture with a compound of formula (I). Alternatively, they can be included in formula (I), such as, for example, dioleylphosphatidyluridinephosphatidylcholine (DOUPC). In this case, they will either play the role of a compound of formula (I) or, in combination with another compound of formula (I), the role of co-lipid.

According to another advantageous aspect, a therapeutic agent identical to or different from that used in step a) is introduced in step d).

Preferably, the functional amphiphilic compound(s) of formula (I) used in step a) is (are) anionic and the functional amphiphilic compound(s) of formula (I) used in step d) is (are) cationic.

Advantageously, a neutral functional amphiphilic compound of formula (I) is used to constitute the outermost lipid layer which can be produced between step d) and step e).

More particularly, the method for preparing the formulations with multiple compartments can comprise the steps implemented under the following general conditions which illustrate, for example, the production of a formulation with multiple compartments in the form of nanoparticles constituted by a solid core containing a therapeutic agent, surrounded by two lipid layers of different polarity formed by compounds of formula (I):

1) Formation of Nanoparticles According to the Invention Comprising a Core Rich in Therapeutic Agent and a First Lipid Layer a compound of formula (I), is dissolved in an organic solvent in order to form a lipid mixture, then the solvent is evaporated off in order to form a first lipid film;

in parallel, the desired quantity of therapeutic agent, preferably an anti-neoplastic agent, is dissolved in distilled water;

the lipid film is rehydrated in the solution of therapeutic agent, preferably an anti-neoplastic agent. A clear solution is obtained by sonication and heating;

the solution is cooled down rapidly, for example by immersion in liquid nitrogen. This heating/cooling cycle is preferably carried out 1 to 10 times, in particular 5 to 10 times, in particular 10 times;

after sonication and centrifugation of the suspension obtained, the supernatant is removed and the pellet is resuspended;

after centrifugation, the pellet is removed and the supernatant is recovered.

2) Formation of Nanoparticles According to the Invention Comprising a Core Rich in Therapeutic Agent and Two Lipid Layers of Different Polarity a second lipid film is prepared from a compound of formula (I) of different polarity from that of the compound of formula (I) used in the first part of the method;

the second lipid film is rehydrated with the supernatant previously recovered, after sonication and centrifugation of the suspension obtained, the supernatant is separated and the pellet resuspended;

after centrifugation, the pellet is removed and the supernatant is recovered, containing the nanoparticles with multiple compartments comprising two lipid layers of different polarity.

Advantageously, the steps of the above method are repeated the number of times necessary to obtain the desired number of lipid layers.

Preferably, the number of lipid layers is comprised between 2 and 6.

Optionally, an additional step consisting of the formation of a lipid layer constituted by at least one functional amphiphilic compound of formula (I) as defined above, said compound of formula (I) being neutral, can be carried out during the $2^{nd}$ part of the method, before the final step allowing the recovery of the nanoparticles with multiple compartments according to the invention.

According to a preferred aspect, during the formation of the lipid mixture in the first part of the preparation described above, or in its second part, at least one co-lipid as defined above is used in addition to the compound of formula (I).

Preferred formulations according to the invention are those in which the first lipid layer is anionic and the second lipid layer is cationic.

The organic solvent can be chosen, for example, from the usual organic solvents in the field, such as, for example, chloroform or dichloromethane, an alcohol such as methanol or ethanol, etc.

The heating is carried out, preferably, to a temperature of the order of 20° C. to 80° C., and the cooling to a temperature of the order of −190° C. (liquid nitrogen) to 0° C. (ice). An appropriate heating/cooling cycle can, for example, be 45° C. for the heating and −78° C. for the cooling.

Preferably, the therapeutic agent is chosen from the platinum complexes (cisplatin, carboplatin, etc.), cisplatin being particularly preferred, or ruthenium which can bind to platinum complexes, or also the inorganic complexes without platinum based on ruthenium II or III, titanium, gallium, cobalt, iron or gold mentioned above.

The molar ratio R of the compound of formula (I)/therapeutic agent can be comprised, for example, between 0.01 and 50, in particular R=0.2

The nanoparticles obtained can optionally be extruded through a polycarbonate filter having, for example, a pore diameter of the order of 100 or 200 nm.

Nanoparticles with multiple compartments are thus obtained, which are constituted by a solid core rich in therapeutic agent (active ingredient) surrounded by at least two lipid layers of different polarity constituted by a functional amphiphilic compound of formula (I) as defined above, with or without co-lipid.

According to an aspect of the method, said lipid mixture contains solely at least one compound of formula (I) and does not contain co-lipid.

The therapeutic agent is preferably used at a concentration of the order of 0.1 ng/mL to 10 mg/mL in the aqueous phase, so that the intracellular delivery of the active ingredient is significant.

Preferred compounds of formula (I) which can be used to form a lipid layer are those in which X represents oxygen.

The compounds of formula (I) in which B represents thymine or adenine are also preferred compounds.

The compounds of formula (I) in which $L_1$, $L_2$ and/or $R_3$ represent a negatively charged group such as, for example, a phosphate, phosphonate, carboxylate, sulphate group, etc., optionally substituted, are preferred compounds for obtaining an anionic lipid layer.

The compounds of formula (I) in which in which $L_1$, $L_2$ and/or $R_3$ represent a negatively charged group such as, for example, an ammonium, phosphonium, imidazolium group, etc., optionally substituted, are preferred compounds for obtaining a cationic lipid layer.

According to a preferred aspect, the invention relates to nanoparticles with multiple compartments as defined above comprising these compounds of formula (I) and a therapeutic agent, in particular an anti-neoplastic agent, in particular the platinum complexes (such as, for example cisplatin, carboplatin, oxaliplatin, nedaplatin, lobaplatin,), or ruthenium capable of binding to platinum complexes, or also the above-mentioned inorganic complexes without platinum based on ruthenium, titanium, gallium, cobalt, iron or gold. Cisplatin is a preferred anti-neoplastic agent for the purposes of the invention.

The compounds of formula (I) can also comprise purine- or pyrimidine-based derivatives having an anti-neoplastic activity, such as, for example, aracytosine (AraC), 5-fluorouracile (5-FU), Iododeoxyuridine (IdU), 2'-deoxy-2'-methylidenecytidine (DMDC) or 5-chloro-6-azido-5,6-dihydro-2'-deoxyuridine.

A subject of the invention is also the use of the nanoparticles with multiple compartments described above, as agents for the transport or targeting of therapeutic agents, in particular of anti-neoplastic agents.

In particular a subject of the invention is also the use of the nanoparticles with multiple compartments described above, as agents for the intracellular delivery of therapeutic agents, in particular of anti-neoplastic agents.

The invention also relates to the use of the nanoparticles with multiple compartments described above, for the preparation of anti-neoplastic medicaments.

The invention also relates to the nanoparticles with multiple compartments described above, for the treatment of tumour diseases, in particular cancers, such as, for example, cancers of the ovary, testicle, colon, cervix, lung, or adenosarcoma etc.

Said nanoparticles with multiple compartments can be obtained by the method described above.

The invention also relates to the pharmaceutical compositions comprising formulations with multiple compartments in the form of nanoparticles constituted by a solid core containing a therapeutic agent, surrounded by at least two lipid layers of different polarity formed from functional amphiphilic molecules or macromolecules (or nanoparticles with multiple compartments), as described above, and a pharmaceutically acceptable vehicle.

The invention is illustrated non-limitatively by the examples below.

All of the starting products originate from suppliers of chemical products (Aldrich, Alfa Aesar and Avanti Polar Lipid) and are used without subsequent purification. The solvents were used without additional distillation. The synthesized compounds were characterized using standard spectroscopic analytical methods such as NMR $^1H$ at 300.13 MHz, $^{13}C$ at 75.46 MHz and $^{31}P$ at 121.49 MHz) and mass spectroscopy (Characteristics). The chemical shifts (δ) in NMR are expressed in ppm and relative to TMS. The coupling constants J in NMR $^1H$ are expressed in Hz. Merck RP-18 F254s plates were used for the thin layer chromatography (TLC). SEPHADEX LH-20 (25-100 μm) silica was used for the purifications by quantitative chromatographies.

The examples below, entitled "Preparation" describe the preparation of synthesis intermediates used for preparing the compounds of formula (I). The preparation of the compounds of formula (I) and the study of the nanoparticles according to the invention are described below in the synthesis examples and the tests entitled "Example".

PREPARATION 1

5'-paratoluenesulphonylthymidine

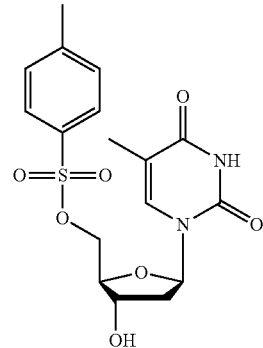

2 g of thymidine (8.26 mmol) in 0.1 M solution is introduced into anhydrous pyridine in a two-necked flask under an anhydrous nitrogen atmosphere. The solution is then cooled down to 0° C. and 3.935 g of paratoluene sulphonic acid chloride (2.5 equivalents, 20.6 mmol) are added by small portions. The reaction medium is left to return to ambient temperature, then stirred for 10 hours. The reaction is then stopped by the addition of 10 mL of methanol, stirring is maintained for 30 min.. 50 mL of $CH_2Cl_2$ is added to the mixture then it is washed successively with 20 mL of a 5% solution of $NaHCO_3$, 20 mL of a saturated solution of NaCl and 20 mL of a 5% solution of $NaHCO_3$. The solvent is eliminated under reduced pressure. The expected compound is obtained pure by recrystallization from methanol.

RF: 0.47 (AcOEt/MeOH 9/1)

Yield: 75%

NMR $^1H$ (300.13 MHz, DMSO $d_6$): δ 1.77 (s, 3H, $CH_3$), δ 2.11 (m, 2H, $CH_2$), δ 2.42 (s, 3H, $CH_3$), δ 3.52 (t. j=6 Hz, 4H, $CH_2$), δ 4.18 (m, 1 H, CH), δ 4.25 (m, 3H, CH, $CH_2$), δ 5.42 (s, 1H, OH), δ 6.15 (t, j=6 Hz, H, CH), δ 7.38 (s, 1 H, CH), δ 7.46 (s, 1H, CH), δ 7.49 (s, 1H, CH), δ 7.78 (s, 1 H, CH), δ 7.81 (s, 1H, CH), δ 11.28 (s, 1H, 1NH).

NMR $^{13}C$ (75.47 MHz, DMSO $d_6$): δ 12.5 ($CH_3$), δ 21.6 ($CH_3$), δ 38.9 ($CH_2$), δ 70.4 ($CH_2$), δ 70.6 (CH), δ 83.7 (CH),

δ 84.5 (CH), δ 110.3 (C), δ 128.1 (ar CH), δ 130.6 (ar 2 CH), δ 132.6 (ar C), δ 136.4 (ar C), δ 145.6 (C), δ 150.8 (C=O), δ 164.1 (C=O).

High resolution MS[M+H]⁺: 397.1

PREPARATION 2

2'-deoxy-5'-toluenesulphonyladenosine

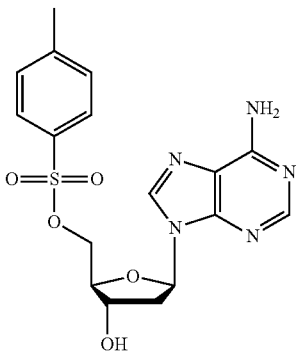

2 g of 2'-deoxyadenosine (8 mmol) in 0.1 M solution is introduced into anhydrous pyridine in a two-necked flask under an anhydrous nitrogen atmosphere. The solution is then cooled down to 0° C. and 3.793 g of paratoluene sulphonic acid chloride (2.5 equivalents, 20 mmol) are added by small portions. The reaction medium is left to return to ambient temperature, then stirred for 10 hours. The reaction is then stopped by the addition of 10 mL of methanol, stirring is maintained for 30 min. 50 mL of CH₂Cl₂ is added to the mixture, then it is washed successively with 20 mL of a 5% solution of NaHCO₃, 20 mL of a saturated solution of NaCl and 20 mL of a 5% solution of NaHCO₃. The solvent is eliminated under reduced pressure. The expected compound is obtained pure by recrystallization from methanol. 2.1 g of a white product is isolated in this way.

RF: 0.37 (AcOEt/MeOH 9/1)
Yield: 63%

PREPARATION 3

5'azido-5'-deoxythymidine

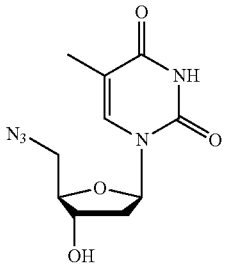

2 g of 5'-paratoluenesulphonylthymidine (5 mmol) as described in Preparation 1 in a 0.1 M solution in DMF is introduced into a two-necked flask provided with a condenser and under an anhydrous nitrogen atmosphere. 1.3 g of sodium azide (4 equivalents, 20 mmol) is added. The solution is then stirred and heated at 110° C. for 10 hours. The mixture is cooled to ambient temperature. 50 mL of CH₂Cl₂ is added to the mixture, then it is washed successively with twice 15 mL of water then with 15 mL of a saturated aqueous solution of NaCl. The organic phase is dried over sodium sulphate then the solvent is eliminated under reduced pressure. The expected compound is obtained pure by recrystallization from methanol. 0.8 g of a white solid is obtained in this way.

RF: 0.47 (AcOEt/MeOH 9/1)
Yield: 60%
MS[M+H]⁺: 268.1

PREPARATION 4

5'-azido-5',2'-dideoxyadenosine

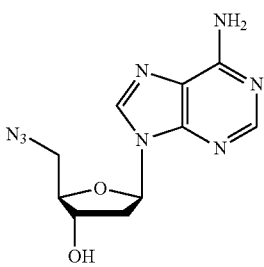

2 g of 2'-deoxy-5'-paratoluenesulphonyladenosine as described in Preparation 2 (5 mmol) in a 0.1 M solution in DMF is introduced into a two-necked flask provided with a condenser and under an anhydrous nitrogen atmosphere. 1.3 g of sodium azide (4 equivalents, 20 mmol) is added. The solution is then stirred and heated at 110° C. for 10 h. The mixture is cooled to ambient temperature. 50 mL of CH₂Cl₂ is added to the mixture then it is washed successively with twice 15 mL of water then with 15 mL of a saturated aqueous solution of NaCl. The organic phase is dried over sodium sulphate then the solvent is eliminated under reduced pressure. The expected compound is obtained pure by recrystallization from methanol. 0.8 g of a white solid is obtained in this way.

RF: 0.37 (AcOEt/MeOH 9/1)
Yield: 60% High resolution MS [M+H]⁺: calculated mass: 277.1161, measured mass: 277.1157

PREPARATION 5

1-propargyloxyoctadecane

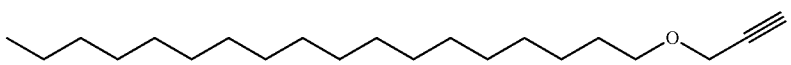 [SMILES: C#CCOCCCCCCCCCCCCCCCCCC]

673 mg of propargyl alcohol (12 mmol) in a 0.5 M solution in DMF is introduced into a clean and dry flask under an anhydrous nitrogen atmosphere. The solution is then cooled down to 0° C. and 180 mg of sodium hydride (0.625 equivalent, 7.5 mmol) are added by small portions. The reaction medium is left to return to ambient temperature. 2 g of 1-bromo-octadecane (0.5 equivalent, 6 mmol) are added. The stirring is maintained for 5 hours. The reaction is then stopped by the addition of 10 mL of methanol and stirring is maintained for 30 min. 50 mL of $CH_2Cl_2$ is added to the mixture then it is washed successively with twice 20 mL of water and 20 mL of a saturated solution of NaCl. The organic phase is then dried over $Na_2SO_4$ then the solvent is eliminated under reduced pressure. The expected compound is obtained pure after separation on a chromatographic column (hexane). 1.2 g of a white product is isolated in this way.

RF: 0.82 (Hexane)

Yield: 65%

NMR $^1$H (300.13 MHz, $CDCl_3$): δ 0.90 (t, j=6 Hz, 3H, $CH_3$), δ 1.28 (s, 3OH, $CH_2$), δ 1.61 (m, 2H, $CH_2$) δ 2.43 (t, j=3 Hz, 1H, CH), δ 3.53 (t, j=6 Hz, 2H, $CH_2$), δ 4.15 (d, j=3 Hz, 2H, $CH_2$).

NMR $^{13}$C (75.47 MHz, $CDCl_3$) NMR $^{13}$C (75.47 MHz, $CDCl_3$): δ 14.2 ($CH_2$), δ 22.7 ($CH_2$) δ 26.1 ($CH_2$) δ 29.4 ($CH_2$) δ 29.6 ($CH_2$), δ 29.6 ($CH_2$), δ 32.0 ($CH_2$), δ 58.0 ($CH_2$), δ 70.4 ($CH_2$), δ 74.1 (CH), δ 80.1 (C).

PREPARATION 6

1,12-propargyloxydodecane 12-propargyloxydodecan-1-ol 1 g of dodecan-1,12-diol (5 mmol) in a 0.5 M solution in DMF is introduced into a clean and dry flask, under an anhydrous nitrogen atmosphere. The solution is then cooled down to 0° C. and 360 mg of hydrogen hydride (3 equivalents, 15 mmol) is added by small portions. The reaction medium is left to return to ambient temperature. 1.49 g of propargyl bromide (2.5 equivalents, 12.5 mmol) is added. The stirring is maintained for 5 hours. The reaction is then stopped by the addition of 10 mL of methanol, stirring is maintained for 30 min. 50 mL of $CH_2Cl_2$ is added to the mixture then it is washed successively with twice 20 mL of water and 20 mL of a saturated solution of NaCl. The organic phase is then dried over $Na_2SO_4$ then the solvent is eliminated under reduced pressure. The products obtained are then separated on a chromatographic column (Hex/ActEth 9/1). Two products are isolated, namely 370 mg of a brown oil corresponding to 1,12-propargyloxydodecane and 430 mg of a brown solid corresponding to 12-propargyloxydodecan-1-ol.

1,12-propargyloxydodecane

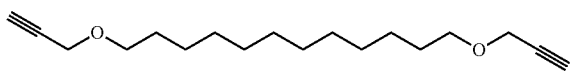 [SMILES: C#CCOCCCCCCCCCCCCOCC#C]

RF: 0.53 (Hexane/AcOtEt 9/1)

Yield: 27%

NMR $^1$H (300.13 MHz, $CDCl_3$): δ 1.31 (m, 16H, $CH_2$), δ 1.61 (m, 4H, $CH_2$), δ 2.43 (t, j=3 Hz, 1H, CH) δ 3.52 (t, j=6 Hz, 4H, $CH_2$), δ 4.15 (d, j=3 Hz, 4H, $CH_2$).

NMR $^{13}$C (75.47 MHz, $CDCl_3$): δ 26.1 ($CH_2$), δ 29.4 ($CH_2$), δ 29.5 ($CH_2$), δ 29.6 ($CH_2$), δ 58.0 ($CH_2$), δ 70.3 ($CH_2$), δ 74.1 (CH), δ 80.1 (C).

12-propargyloxydodecan-1-ol

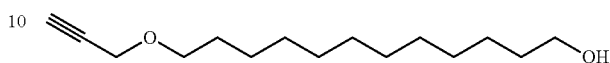

RF: 0.10 (Hexane/AcOtEt 9/1)

Yield: 36%

NMR $^1$H (300.13 MHz, $CDCl_3$): δ 1.32 (m, 16H, $CH_2$), δ 1.59 (m, 4H, $CH_2$), δ 2.43 (t, j=3 Hz, 2H, CH), δ 3.52 (t, j=6 Hz, 2H, $CH_2$), δ 3.65 (t, j=6 Hz, 2H, $CH_2$), δ 4.15 (d, j=3 Hz, 2H, $CH_2$).

NMR $^{13}$C (75.47 MHz, $CDCl_3$): δ 25.8 ($CH_2$), δ 26.0 ($CH_2$), δ 29.4 (2 $CH_2$), δ 29.5 (2 $CH_2$), δ 29.6 ($CH_2$), δ 32.7 ($CH_2$), δ 57.9 ($CH_2$), δ 62.7 ($CH_2$), δ 70.2 ($CH_2$), δ 74.2 (CH), δ 79.9 (C).

PREPARATION 7 o-propargylcholesterol

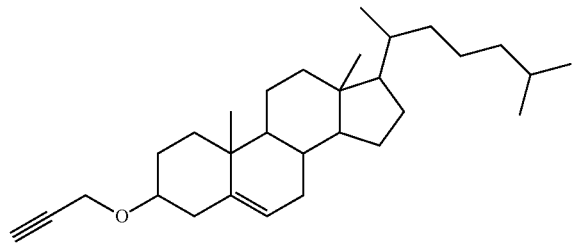 [SMILES: C#CCOC1CCC2(C)C(=CCC3C2CCC2(C)C(C(C)CCCC(C)C)CCC32)C1]

500 mg of cholesterol (1.3 mmol) in a 0.5 M solution in DMF is introduced into a clean and dry flask, under an anhydrous nitrogen atmosphere. The solution is then cooled down to 0° C. and 47 mg of sodium hydride (1.5 equivalents, 2 mmol) is added by small portions. The reaction medium is left to return to ambient temperature. 238 mg of propargyl bromide (1.5 equivalents, 2 mmol) is added. The stirring is maintained for 5 hours. The reaction is then stopped by the addition of 10 mL of methanol and the stirring is maintained for 30 min. 50 mL of $CH_2Cl_2$ is added to the mixture then it is washed successively with twice 20 mL of water and 20 mL of a saturated solution of NaCl. The organic phase is then dried over Na2SO4 then the solvent is eliminated under reduced pressure. The expected compound is obtained after purification on a chromatographic column (Hexane/AcOEt 8/2). 215 mg of a white product is isolated in this way.

RF: 0.83 (Hexane/AcOEt 8/2)

Yield: 39

EXAMPLE 1

Thymidine 3'-(1,2-dimyristoyl-sn-glycero-3-phosphate) (di c14dT)

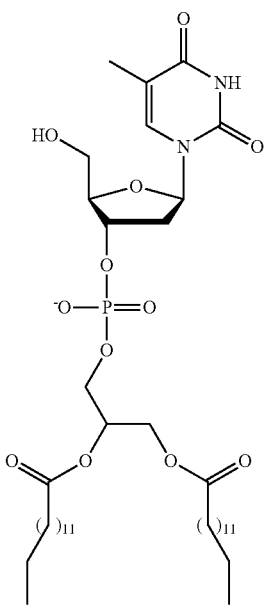

5'-O-(4,4'-dimethoxytrityl)-2'-deoxythymidine,3'-[(2-cyano-ethyl)-N,N-diisopropyl)]phosphoramidite (0.500 g, 1 eq, 0.67 mmol), 1,2-dimyristoyl-sn-glycerol (0.447 g, 1.3 eq, 0.87 mmol) and a 0.45 M solution of tetrazole in acetonitrile (2 mL, 1.3 eq, 0.87 mmol) are dissolved in 4 mL of anhydrous acetonitrile under nitrogen. The reaction medium is magnetically stirred for 24 hours at ambient temperature. The mixture is then oxidized by the addition of 43 mL of a 0.02M solution of diiodine in THF/Pyr/$H_2O$. After 12 hours at ambient temperature, the solvent is evaporated off under vacuum. The residue is dissolved in 8 mL of dichloromethane. Then, 0.2 mL of 1,5-diazabicyclo[5.4.0]undec-7-ene (DBU) (1.3 eq, 0.87 mmol) is added to the reaction medium over 5 hours. The reaction medium is washed with a 0.1N solution of HCl then with a saturated solution of $Na_2S_2O_7$. The organic phase is concentrated under vacuum. The compound is obtained after purification by flash chromatography (381 mg) using an elution gradient (MeOH/DCM 9:1 to 1:1).

Yield: 69%

Rf: 0.34 (DCM/MeOH 9:1)

NMR $^1$H (300 MHz, $CDCl_3$): δ in ppm 0.84 (t, 6H, J=6.92 Hz, 2*$CH_3$), 1.21 (m, 40H, 20*$CH_2$), 1.42 (dd, 4H, J1=8.45 Hz, J2=15.68 Hz, 2*$CH_2$), 1.89 (s, 3H, Me), 2.30 (dd, 4H, J1=7.43 Hz, J2=15.92 Hz, 2*$CH_2$), 2.83 (t, 2H1 J=5.84, H2'), 3.84 (m, 1H, $H_3$'), 4.09-4.35 (m, 7H, 2*$CH_2$(glycerol), H4', H5'), 5.27 (s, 1H, CHglycerol), 6.22 (t, 1 H, J=6.81 Hz, H1'), 7.61 (s, 1H, Hbase).

NMR $^{13}$C (75 MHz, $CDCl_3$): δ in ppm 19.29 ($CH_3$), 23.71 ($CH_2$), 26.57 ($CH_2$), 28.73 ($CH_2$), 32.76 ($CH_2$), 37.85 ($CH_2$), 48.90 ($CH_2$), 166.15 (C=O).

NMR $^{31}$P (121 MHz, $CDCl_3$): δ in ppm 0.61.

High Resolution Mass FAB—theoretical m/z=815.4823 observed m/z=815.4794.

EXAMPLE 2

Thymidine 3'-(1,2-dipalmitoyl-sn-glycero-3-phosphate) (di c16dT)

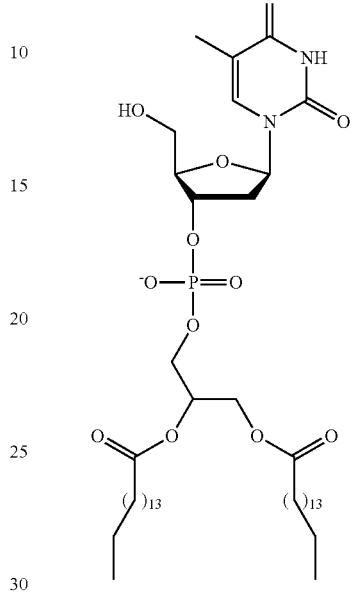

5'-O-(4,4'-dimethoxytrityl)-2'-deoxythymidine,3'-[(2-cyano-ethyl)-N,N-diisopropyl)]phosphoramidite (0.500 g, 1 eq, 0.67 mmol), 1,2- dipalmitoyl-sn-glycerol (0.496 g, 1.3 eq, 0.87 mmol / solubilized in 3 mL of THF) and a 0.45 M solution of tetrazole in acetonitrile (2 mL, 1.3 eq, 0.87 mmol) are dissolved in 3 mL of anhydrous acetonitrile under nitrogen. The reaction medium is magnetically stirred for 24 hours at ambient temperature and under nitrogen. The mixture is then oxidized by the addition of 43 mL of a 0.02M solution of diiodine in THF/Pyr/$H_2O$. After 12 hours at ambient temperature, the solvent is evaporated off under vacuum and dried under $P_2O_5$ overnight using a pump. The residue is dissolved in 8 mL of dichloromethane. Then, 0.2 mL of 1,5-diazabicyclo[5.4.0]undec-7-ene (DBU) (1.3 eq, 0.87 mmol) is added to the reaction medium over 5 hours. The reaction medium is washed with a 0.1N solution of HCl then with a saturated solution of $Na_2S_2O_3$. The organic phase is concentrated under vacuum. The compound is obtained after purification by flash chromatography (180 mg) using an elution gradient (MeOH/DCM 98:2 to 1:1).

Yield: 24%

Rf: 0.3 (DCM/MeOH 8:2)

NMR $^1$H (300 MHz, $CDCl_3$): δ in ppm 0.88 (t, 6H, J=6.9 Hz, 2*CH3), 1.25 (m, 48H, 24*$CH_2$), 1.42 (dd, 4H, J1=8.4 Hz, J2=15.6 Hz1 2*$CH_2$), 1.90 (s, 3H, Me), 2.33 (m, 4H, 2*$CH_2$), 2.83 (t, 2H, J=5.6 Hz, $H_2$'), 3.84 (m, 1H, H3'), 4.09-4.35 (m, 7H, 2*$CH_2$(glycerol), $H_4$', $H_5$'), 5.27 (s, 1H, CH glycerol), 6.21 (t, 1H, J=6.7 Hz, HT), 7.54 (s, 1H, H base).

NMR $^{13}$C (75 MHz, $CDCl_3$): δ in ppm 12.4 ($CH_3$ base), 14.1 ($CH_3$ chain), 19.6 ($CH_2$), 19.7 ($CH_2$), 22.6 ($CH_2$), 24.8 ($CH_2$), 29.1-29.6 ($CH_2$), 31.9 ($CH_2$), 33.9 ($CH_2$), 34.1 ($CH_2$), 61.5 ($CH_2$), 61.7 ($CH_2$), 62.5 ($CH_2$), 62.6 ($CH_2$), 66.1($CH_2$), 66.2 ($CH_2$), 69.1 (CH), 78.8 (CH), 85.5 (CH), 86.1 (CH), 111.3 (C base), 136.8 (CH base), 150.5 (O=O base), 164.1 (O=O base), 173.0 (O=O chain), 173.5 (O=O chain).

NMR $^{31}$P (121 MHz, $CDCl_3$): δ in ppm 2.1.

Mass ESI-: theoretical m/z=872.5 observed m/z =871.3.

EXAMPLE 3

5'-(4-Hexadecyloxymethyl-[1,2,3]triazol-1-yl)-5', 2'dideoxythymidine

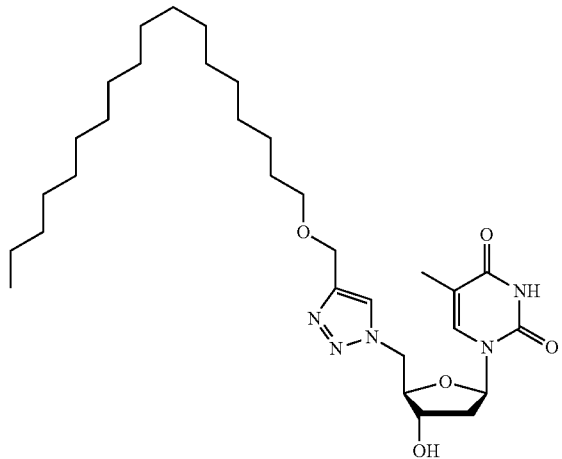

200 mg of 5'-azido-5'-deoxythymidine as described in Preparation 3 (0.75 mmol) and 231 mg of 1-propargyloxyoctadecane as described in Preparation 5 (1 equivalent) in a 0.1 M solution in a mixture of THF and water (1/1) are introduced into a flask. Then, the following are added successively: 30 mg of sodium ascorbate (0.2 equivalents, 0.15 mmol) and 12 mg of copper sulphate (0.1 equivalent, 0.075 mmol). The reaction medium is stirred and heated at 60° C. for 5 hours. The mixture is then cooled down to ambient temperature. The reaction medium is immediately adsorbed on silica and the solvent evaporated off. 180 mg of a white solid is obtained after chromatography on a silica column (AcOEt/MeOH 8/2).

RF: 0.72 (AcOEt/MeOH 8/2)
Yield: 42%
High resolution MS [M+H]$^+$: calculated mass: 576.4125, measured mass: 576.4120

EXAMPLE 4

5'-(4-Hexadecyloxymethyl-[1,2,3]triazol-1-yl)-5',2'-dideoxyadenosine

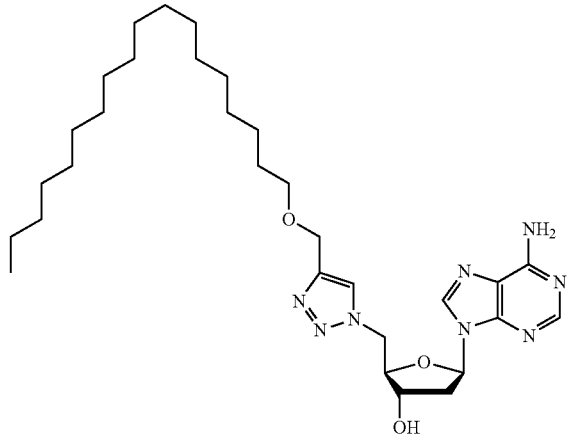

200 mg of 5'-azido-5',2'-dideoxyadenosine as described in Preparation 4 (0.72 mmol) and 223 mg of 1-propargyloxyoctadecane as described in Preparation 5 (1 equivalent) in a 0.1 M solution in a mixture of THF and water (1/1) are introduced into a flask. Then, the following are added successively: 30 mg of sodium ascorbate (0.2 equivalents, 0.15 mmol) and 12 mg of copper sulphate (0.1 equivalent, 0.075 mmol). The reaction medium is stirred and heated at 60° C. for 5 hours, then the mixture is cooled down to ambient temperature. The reaction medium is immediately adsorbed on silica and the solvent evaporated off. 150 mg of a white solid is obtained after column chromatography (AcOEt/MeOH 8/2).

RF: 0.65 (AcOEt/MeOH 8/2)
Yield: 35%
NMR $^1$H (300.13 MHz, CDCl$_3$): δ 0.89 (t, j=6 Hz, 3H, CH$_3$), δ 1.26 (m, 3OH, CH$_2$), δ 1.55 (m, 2H, CH$_2$), δ 2.54 (m, 1H, CH$_2$), δ 3.06 (m, 1H, CH$_2$), δ 3.45 (t, j=6 Hz, 2H, CH$_2$), δ 4.50 (m, 4H, CH$_2$, CH), δ 4.89 (m, ???), δ 5.88 (s, 2H, NH$_2$), δ 6.40 (t, j=6 Hz, 1H, CH), δ 7.42 (s, 1H, CH), δ 7.81 (s, 1H, CH), δ 8.35 (s, 1H, CH).

High resolution MS [M+H]$^+$: calculated mass: 585.4241, measured mass: 585.4254

EXAMPLE 5

5'-(4-((O-cholesteryl)-methyl)-[1,2,3]triazol-1-yl)-5', 2'dideoxythymidine

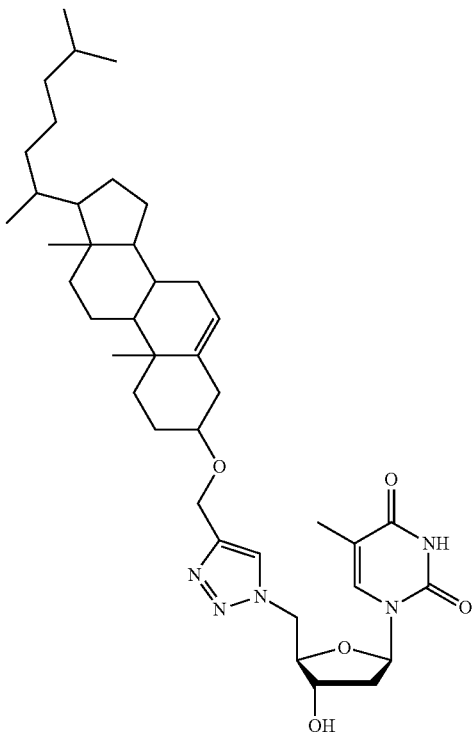

170 mg of 5'-azido-5'-deoxythymidine as described in Preparation 3 (0.63 mmol) and 270 mg of o-propargylcholesterol as described in Preparation 7 (1 equivalent) in a 0.1 M solution in a THF/water mixture (1/1) are introduced into a flask. The following are added successively: 20 mg of sodium ascorbate (0.2 equivalent, 0.13 mmol) and 10 mg of copper sulphate (0.1 equivalent, 0.063 mmol). The reaction medium is stirred and heated at 60° C. for 5 hours. The mixture is cooled down to ambient temperature. The reaction medium is immediately adsorbed on silica and the solvent evaporated off. The compound is obtained pure by column chromatography (AcOEt/MeOH 8/2). 260 mg of a white solid are obtained.

RF: 0.57 (AcOEt/MeOH 8/2)
Yield: 59%
MS [M+H]$^+$: 692.3

EXAMPLE 6

1,12-bis-[5'-(4-(methyl)-[1,2,3]triazol-1-yl)-5', 2'dideoxythymidine]-oxydodecane

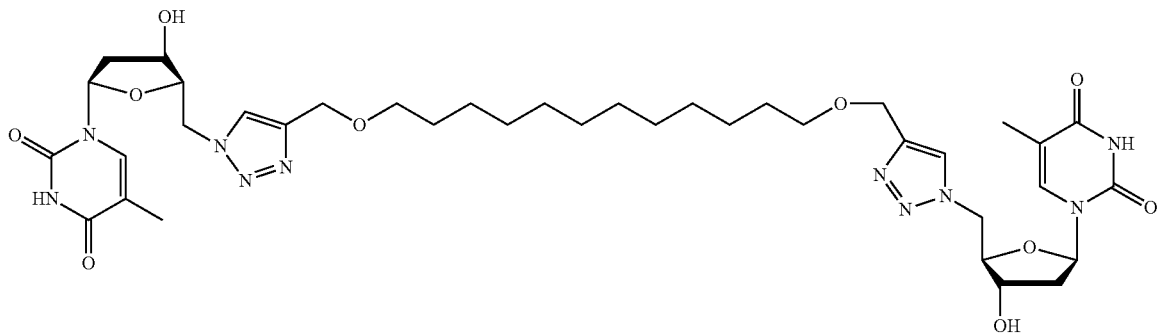

100 mg of 5'-azido-5'-deoxythymidine as described in Preparation 3 (0.375 mmol) and 52 mg of 1,12-dipropargyloxydodecane prepared from the compound described in Preparation 6 (0.5 equivalent) in a 0.1 M solution in a THF/water mixture (1/1) are introduced into a flask. The following are added successively: 15 mg of sodium ascorbate (0.2 equivalent, 0.075 mmol) and 6 mg of copper sulphate (0.1 equivalent, 0.0375 mmol). The reaction medium is stirred and heated at 60° C. for 5 hours. The mixture is then cooled down to ambient temperature. The reaction medium is immediately adsorbed on silica and the solvent evaporated off. The compound is obtained pure by column chromatography (AcOEt/MeOH 8/2). 90 mg of a white solid is obtained.

Yield: 59

NMR $^1$H (300.13 MHz, MeOH d$_4$): δ 1.28 (m, 16H, CH$_2$), δ 0.83 (m, 4H, CH$_2$), δ 1.89 (s, 6H, CH$_3$), δ 2.17 (s, 2H, CH$_2$), δ 2.25 (m, 4H, CH$_2$), δ 3.51 (t, j=6 Hz, 4H, CH$_2$), δ 4.18 (m, 2H, CH) δ 4.42 (m, 2H, OH) δ 4.58 (s, 4H, CH$_2$), δ 4.76 (qd, j=6 Hz, 4H, CH$_2$), δ 6.21 (t, j=6 Hz, 2H, CH), δ 7.23 (s, 2H, CH), δ 7.99 (s, 2H, CH).

EXAMPLE 7

5'-(4-(1(R;-hydroxy-hexyl)-[1,2,3]triazol-1-yl)-5', 2'dideoxythymidine

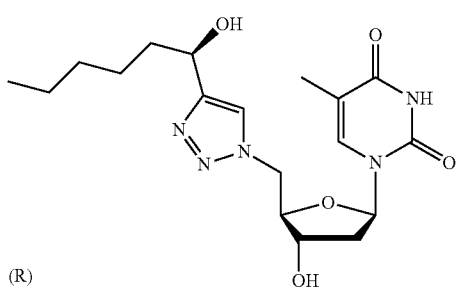

215 mg of 5'-azido-5'-deoxythymidine as described in Preparation 3 (0.8 mmol) and 101.5 mg of (R) oct-1-yn-3-ol (1 equivalent) in a 0.1 M solution in a THF/water mixture (1/1) are introduced into a flask. The following are added successively: 31.5 mg of sodium ascorbate (0.2 equivalent, 0.15 mmol) and 13 mg of copper sulphate (0.1 equivalent, 0.075 mmol). The reaction medium is stirred and heated at 60° C. for 5 hours. The mixture is then cooled down to ambient temperature. The reaction medium is then immediately adsorbed on silica and the solvent evaporated off. The compound is obtained pure by column chromatography (AcEt/MeOH 9/1). 240 mg of a white solid is obtained.

RF: 0.48 (AcEt/MeOH 9/1)

Yield: 76%

High resolution MS [M+H]$^+$: calculated mass: 576.4125, measured mass: 576.4120

EXAMPLE 8

5'-(4-(1-(S)-hydroxy-hexyl)-[1,2,3]triazol-1-yl)-5'2'dideoxythymidine

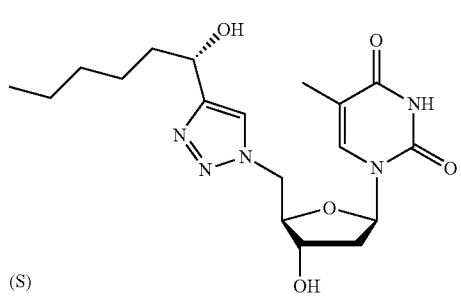

215 mg of 5'-azido-5'-deoxythymidine as described in Preparation 3 (0.8 mmol) and 101.5 mg of (S) oct-1-yn-3-ol (1 equivalent) in a 0.1 M solution in a THF/water mixture (1/1) are introduced into a flask. The following are added successively: 31.5 mg of sodium ascorbate (0.2 equivalent, 0.15 mmol) and 13 mg of copper sulphate (0.1 equivalent, 0.075 mmol). The reaction medium is stirred and heated at 60° C. for 5 hours. The mixture is then cooled down to ambient temperature. The reaction medium is then immediately adsorbed on silica and the solvent evaporated off. The compound is obtained pure by column chromatography (AcOEt/MeOH 85/15). 255 mg of a white solid is obtained.

RF: 0.48 (AcOEt/MeOH 85/15)

Yield: 78%

High resolution MS [M+H]⁺: calculated mass: 576.4125, measured mass: 576.4120

EXAMPLE 9

5'-(4-(1-hydroxy-hexyl)-[1,2,3]triazol-1-yl)-5', 2'dideoxyadenosine

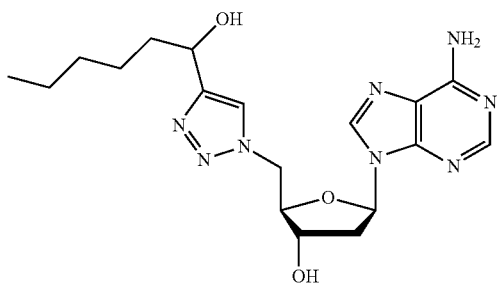

200 mg of 5'-azido-5'-deoxythymidine as described in Preparation 3 (0.75 mmol) and 95 mg of the racemic mixture of oct-1-yn-3-ol (1 equivalent) in a 0.1 M solution in a THF/water mixture (1/1) are introduced into a flask. The following are added successively: 30 mg of sodium ascorbate (0.2 equivalent, 0.15 mmol) and 12 mg of copper sulphate (0.1 equivalent, 0.075 mmol). The reaction medium is stirred and heated at 60° C. for 5 hours. The mixture is then cooled down to ambient temperature. The reaction medium is immediately adsorbed on silica and the solvent evaporated off. The compound is obtained pure by column chromatography (AcOEt/MeOH 8/2). 240 mg of a white solid is obtained.

RF: 0.47 (AcOEt/MeOH 8/2)
Yield: 80%
High resolution MS [M+H]⁺: calculated mass: 576.4125, measured mass: 576.4120

EXAMPLE 10

Preparation of the Nanoparticles With Multiple Compartments

The compound thymidine 3'-(1,2-dipalmitoyl-sn-glycero-3-phosphate) (di C16 dT) prepared in Example 2 was used as anionic compound of formula (I), dioleylphosphatidylcholine (DOPC) as co-lipid and the compound (N[5'-(2',3'-dioleoyl)uridine]-N',N',N'-trimethylammonium tosylate) (DOTAU) prepared as described in Pauline Chabaud et al., Bioconjugate Chem., 2006, 17, 466-472 as cationic compound of formula (I).

1) Preparation of the Stock Solutions
a) Preparation of the cisplatin solution:
15 mg of cisplatin is solubilized in 10 mL of milli-Q water (final concentration: 5 mM). This suspension is stirred for 1 min (vortex), then incubated at 37° C. for 24 hours.
b) Preparation of the lipid solutions:
Solution A: 20 mg of diC16dT are solubilized in 2 mL of dichloromethane (10 mg/mL). This sample is stored at −20° C.
Solution B: DOPC: solution at 20 mg/mL in dichloromethane stored at −20° C.
Solution C: DOTAU: solution at 20 mg/mL in dichloromethane stored at −20° C.

2) Preparation of the Lipid Formulation for the First Layer
52.3 µL of solution A is mixed with 47.2 µL of solution B in a 2 mL Eppendorf® tube. These volumes correspond to a molar ratio of the two lipids of 1/1.
The dichloromethane is evaporated off under nitrogen in order to obtain a homogeneous lipid film.
3) Preparation of the Nanoparticles (First Anionic Lipid Layer)
1.2 mL of the cisplatin solution pre-incubated at 37° C. are used to rehydrate the lipid film prepared beforehand. The mixture is incubated at ambient temperature overnight. A series of 10 heating (water bath at 55° C.) and freezing (dry ice/methanol −72° C.) cycles is carried out.
4) Washing and Recovery of the Nanoparticles Comprising a First Anionic Lipid Layer
Once the series of 10 cycles is completed, the suspension is stirred and placed in a glass haemolysis tube, then subjected to sonication for 7 min. After sonication, the suspension is centrifuged at 10,000 rpm/5 min/20° C. The supernatant is discarded and the nanoparticle pellet is resuspended in 1 mL of milli-Q water. This step is repeated a second time.
The suspension is centrifuged at 1000 rpm/2.5 min/20° C. The pellet is discarded and the supernatant contains the anionic nanoparticles.
The zeta potential, measured according to the technique described in Andrea Mayer et al. Toxicology, 2009, 258, 139-147 or K. Furusawa and K. Uchiyama, 1988, 140, 217-226, is −43.3±6 mV.
5) Preparation of the Nanoparticles Comprising a First Anionic Lipid Layer and a Second Cationic Lipid Layer
180 µL of the solution C is deposited in a 2 mL Eppendorf® tube. The dichloromethane is evaporated off with compressed nitrogen in order to obtain a homogeneous lipid film.
6) Washing and Recovery of the Nanoparticles With Multiple Compartments (Cationic Surface Layer)
The cationic lipid film is rehydrated with the suspension of the anionic nanoparticles prepared in step 4).
Vortex stirring was carried out for 5 min followed by sonication for one minute.
The suspension is centrifuged at 10,000 rpm for 5 min at 20° C. in order to remove the lipids not bound to the nanoparticles. The supernatant is removed then the pellet is rehydrated with 1 mL of milli-Q water.
The suspension is centrifuged at 1000 rpm/2.5 min/20° C. The pellet is discarded and the supernatant contains the multi-compartment nanoparticles with a cationic surface layer.
The zeta potential, measured as previously, is 42.3±8 mV.

EXAMPLE 11

Stability Test (% of Cisplatin Released)

The nanoparticles prepared according to the protocol of Example 10 are assayed by ICP optical spectrometry (the measured value corresponds to the total concentration). The suspension of the nanoparticles is aliquoted into 5 Eppendorf® tubes (150 µL). The latter are incubated at 37° C. under stirring (300 rpm) for different periods of time (0, 2.5, 5, 10 and 24 hours).
At a given time (x), the tube is centrifuged at 14,000 rpm/10 min/20° C. and 50 µL of supernatant (recovered carefully so as not to resuspend the pellet) is assayed.
Nanoparticles based on 1,2-dioleoyl-sn-glycero-3-[phospho-L-serine] (DOPS) with 1,2-dioleoyl-sn-glycero-3-phosphocholine (DOPC) as a co-lipid are prepared according to the same protocol as a comparison. These nanoparticles comprise a single anionic lipid layer.

The percentage release of cisplatin is calculated according to the following equation:

% of cisplatin released=$Cx-C0/Ct-C0$

Cx: concentration found at a given time (x).
C0. concentration found in the supernatant before incubation.
Ct: total concentration found without incubation and without centrifugation.

The curve of the release of cisplatin as a function of the incubation time is shown in FIG. 1.

The nanoparticles comprising a single anionic lipid layer obtained at the end of step 4 of Example 10 (denoted NP−) are represented by the symbol -♦-, the nanoparticles according to the invention (denoted NP+) comprising a first anionic lipid layer and a second cationic lipid layer obtained at the end of step 6 of Example 10 are represented by the symbol -■- and the nanoparticles based on DOPC/DOPS (denoted PS) by the symbol -▲-

The results show that the half life (incubation time necessary to release 50% of the cisplatin) is greater than 24 hours for the NP+ nanoparticles according to the invention, whereas it is of the order of 6.5 hours for the nanoparticles based on DOPC/DOPS.

Moreover, after the same incubation time (6.5 hours), it is observed that the nanoparticles NP− (monolayer) have released more than 30% of their cisplatin content, whereas the NP+ nanoparticles according to the invention have released less than 20% of their cisplatin, which emphasizes the remarkable stability properties of the NP+ nanoparticles at 37° C.

EXAMPLE 12

Stability Test (% of Cisplatin Released) in the Presence of Foetal Calf Serum The nanoparticles prepared according to the protocol of Example 10 are assayed by ICP optical spectrometry (the measured value corresponds to the total concentration). The suspension of the nanoparticles is aliquoted into 5 Eppendorf® tubes (150 µL). The latter are centrifuged at 10,000 rpm for 5 min at 20° C. 50 µL of the supernatant is assayed by ICP optical spectrometry and the remaining 100 µL is separated. The pellet containing the nanoparticles is rehydrated with 150 µL of foetal calf serum (FCS, ref Invitrogen 10270-106). The samples are incubated at 37° C. under stirring (300 rpm) for different periods of time (0, 2.5, 5, 10 and 24 hours).

At a given time (x), the tube is centrifuged at 14,000 rpm/10 min/20° C. and 50 µL of supernatant (recovered carefully so as not to resuspend the pellet) are assayed.

Nanoparticles based on 1,2-dioleoyl-sn-glycero-3-[phospho-L-serine] (DOPS) with 1,2-dioleoyl-sn-glycero-3-phosphocholine (DOPC) as a co-lipid are prepared according to the same protocol as a comparison.

The percentage release of cisplatin is calculated according to the following equation:

% of cisplatin released=$Cx-C0/Ct-C0$

Cx: concentration found at a given time (x).
C0: concentration found in the supernatant before incubation and before contact with the FCS.
Ct: total concentration found without incubation and without centrifugation.

Figure 2:
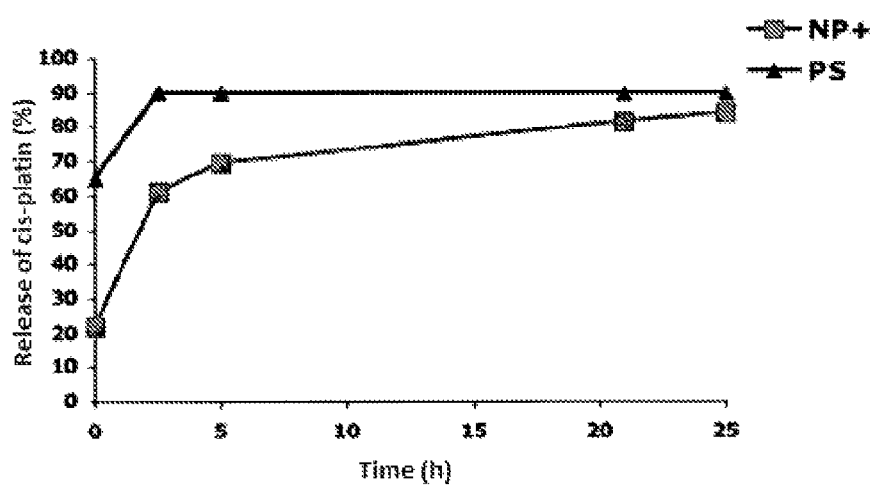
FIG. 2 shows the curve of the release of cisplatin as a function of the incubation time. The nanoparticles representing an embodiment of the invention (denoted NP+) comprising a first anionic lipid layer and a second cationic lipid layer obtained in Example 10 are compared to the nanoparticles based on DOPC/DOPS (denoted PS).

The curve of the release of cisplatin as a function of the incubation time is shown in FIG. 2.

The nanoparticles according to the invention (denoted NP+) comprising a first anionic lipid layer and a second cationic lipid layer obtained in Example 10 are represented by the symbol -■- and the nanoparticles based on DOPC/DOPS (denoted PS) by the symbol -▲-

The results show that the incubation time necessary to release 90% of the cisplatin is greater than 24 hours for the NP+ nanoparticles according to the invention, whereas it is less than 2 hours for the PS nanoparticles.

EXAMPLE 13

Assay of Intracellular Cisplatin

Protocol

IGROV1 cells (cisplatin-sensitive ovarian adenocarcinoma line) at 80% confluence (dish 10 cm in diameter) are treated with 100 µm of free cisplatin or cisplatin encapsulated in the nanoparticles of Example 10 for 2, 4 or 6 hours. On completion of this treatment two washings with PBS are carried out. The cells are treated with trypsin and resuspended in PBS. Two washings of the cell suspensions with PBS are carried out (centrifugation 1000 rpm/1 min). The cells are suspended in 1 mL of PBS and counted.

The same procedure is followed with SKV03 cells (cisplatin-resistant ovarian adenocarcinoma line).

ICP Optical Assay $10^6$ cells are lysed with 500 µL of the cell lysis solution (lysis buffer from SIGMA). The volume is topped up to 5 mL with milli-Q water with 1% $HNO_3$ acid.

Results

The results are represented in FIG. 3, which shows the concentration of cisplatin released after cell lysis (expressed in nanomole/$10^6$ cells/100 µM of treatment) as a function of time, corresponding to the concentration of cisplatin internalized in the treated cells.

The columns hatched vertically (on the left), horizontally (centre) and chequered (on the right) correspond to a treatment of the cells over 2 hours, 4 hours and 6 hours respectively.

The results show that the internalization of cisplatin is clearly more effective in the presence of the nanoparticles according to the invention (denoted NP+) comprising a first anionic lipid layer and a second cationic lipid layer obtained in Example 10 than in the case of the PS nanoparticles and free cisplatin.

Figure 3A:
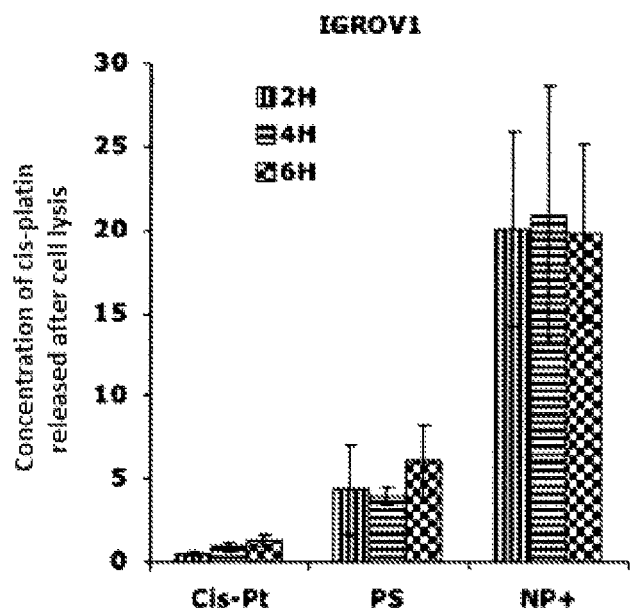
FIGS. 3A and 3B show the concentration of cisplatin released after cell lysis (expressed in nanomole/$10^6$ cells/100 µM) as a function of time for IGROV1 cells (cisplatin-sensitive ovarian adenocarcinoma line.

For example, under identical conditions ($10^6$ IGROV1 cells, 100 µM, 2 hours) 0.5 nanomole of cisplatin is internalized in the case of the free cisplatin whereas the internalization is 40 times greater (20 nanomoles) in the case of the NP+ nanoparticles according to the invention (FIG. 3A).

Figure 3B:
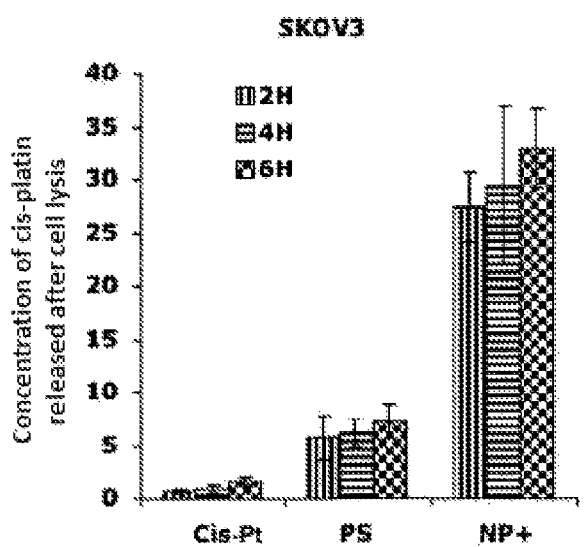

As regards the cisplatin-resistant cell line SKOV3, under identical conditions ($10^6$ cells SKOV3, 100 µM, 2 hours), the internalization is 60 times greater (30 nanomoles) in the case of the NP+ nanoparticles according to the invention than in the case of the free cisplatin (0.5 nanomole) (FIG. 3B).

EXAMPLE 14

Study of the Cytotoxic Effects of the Nanoparticles With Multiple Compartments on Different Tumor Lines Protocol
a/Preparation and Treatment of the Cells:

The study consists of determining the concentration inhibiting 50% of cell proliferation ($IC_{50}$) on a panel of tumor lines, namely cisplatin-sensitive A2780 (Human ovarian carcinoma epithelial tumor) and cisplatin-resistant A2780/CisPt (Human ovarian carcinoma epithelial tumor)

cisplatin-sensitive IGROV-1 (Human ovarian carcinoma) and cisplatin-resistant IGROV-1/CisPt (Human ovarian carcinoma)

cisplatin-sensitive L1210 (mouse lymphocytic leukemia) and cisplatin-resistant L1210/CisPt (mouse lymphocytic leukemia) (human leukemia)

NIH: OVCAR3 (ovarian carcinoma), and

P388 (mouse lymphoma)

Figure 4:
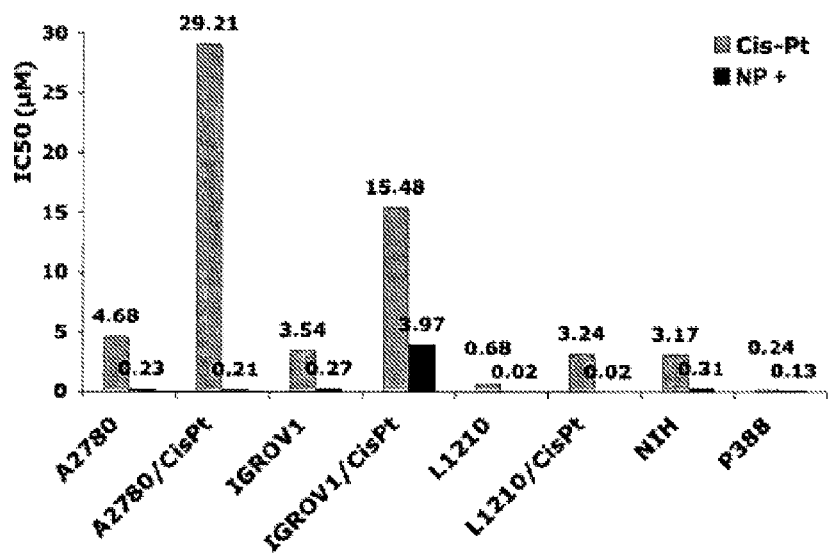
FIG. 4 shows a graph of the concentration necessary to obtain 50% cell death (IC50) on different tumor lines treated with free cisplatin or with the nanoparticles according to the invention comprising a first anionic lipid layer and a second cationic lipid layer obtained at the end of step 6 of Example 10 (denoted NP+) and containing cisplatin.

2500 cells (ovarian adenocarcinoma lines, etc.) per well are incubated in 100 µL of the medium with serum in a 96-well plate. After 24 hours the medium is aspirated and the cells are treated with free cisplatin or cisplatin encapsulated in the nanoparticles of Example 10 in 100 µL of the medium without serum at different concentrations (500, 100, 10, 1, 0.1, 0.01, 0.001 µM). After treatment for 24 hours, the medium is removed and the cells are washed twice with 100 µL of PBS then incubated with 100 µL of the medium with serum.

b/Revelation of the Toxicity:

48 hours after the two washings, the cell viability is revealed by adding 20 µL of MTS. The absorbance at 490 nm is measured after incubation for 2 to 4 hours at 37° C. The absorbance is proportional to the cell viability.

c/Results:

The results are shown in FIG. 4 which shows the concentration necessary to obtain 50% cell death (IC50) with free cisplatin (light grey column on the left) or the nanoparticles according to the invention comprising a first anionic lipid layer and a second cationic lipid layer obtained at the end of step 6 of Example 10 (denoted NP+) containing cisplatin (dark grey column on the right).

The results show that the nanoparticles according to the invention are more effective than free cisplatin in all the cisplatin-sensitive or -resistant cell lines studied.

For example, in the case of the cisplatin-sensitive cell line A2780, 50% cell death is obtained with 0.23 µM of nanoparticles according to the invention whereas 4.68 µM of free cisplatin must be used to obtain the same mortality.

On the cisplatin-resistant line A2780, 50% cell death is obtained with 0.21 µM of nanoparticles according to the invention as against 29.21 µM of free cisplatin. In this case the nanoparticles according to the invention are respectively 18 and 140 times more effective than the free cisplatin on the sensitive line A2780 and resistant line A2780.

EXAMPLE 15

Study of the Cytotoxic Effects of the Nanoparticles With Multiple Compartments on the Tumor Lines IGROV-1 and SKOV3

Protocol a/Preparation and Treatment of the Cells:

2500 cells (IGROV1, SKOV3, ovarian adenocarcinoma lines) per well are incubated in 100 µL of the medium with serum in a 96-well plate. After 24 hours the medium is aspirated and the cells are treated with free cisplatin or cisplatin encapsulated in the nanoparticles of Example 10 in 100 µL of the medium without serum at different concentrations (500, 100, 10, 1, 0.1, 0.01, 0.001 µM). After treatment for 24 hours, the medium is removed and the cells are washed twice with 100 µL of PBS then incubated with 100 µL of the medium with serum.

b/Revelation of the Toxicity:

48 hours after the two washings, the cell viability is revealed by adding 20 µL of MTS. The absorbance at 490 nm is measured after incubation for 2 to 4 hours at 37° C. The absorbance is proportional to the cell viability.

c/Results:

The results are represented in FIG. 5, which shows the concentration necessary to obtain 50% cell death (IC50) with free cisplatin (column 1, on the left), the control nanoparticles based on DOPC/DOPS (denoted PS) (column 2, left of centre), the nanoparticles comprising a single anionic lipid layer obtained at the end of step 4 of Example 10 (denoted NP−) (column 3, right of centre) and the nanoparticles according to the invention (denoted NP+) comprising a first anionic lipid layer and a second cationic lipid layer obtained at the end of step 6 of Example 10 (column on the right).

Figure 5A:
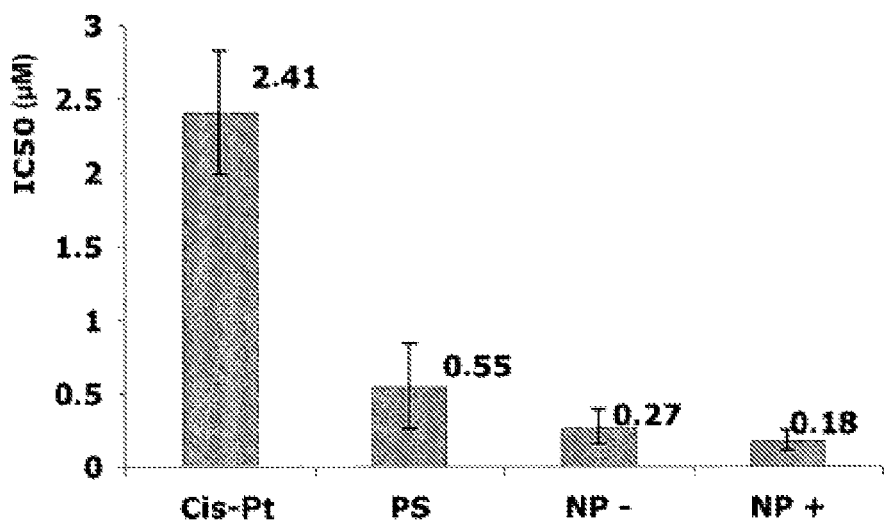
FIGS. 5A and 5B show a graph of the concentration necessary to obtain 50% cell death (IC50) on different tumor lines, IGROV1 (FIG. 5A) and SKOV3 (FIG. 5B), treated with free cisplatin, with control nanoparticles based on DOPC/DOPS (denoted PS), or with nanoparticles comprising a single anionic lipid layer obtained at the end of step 4 of example 10 (denoted NP−), or with nanoparticles according to the invention (denoted NP+) comprising a first anionic lipid layer and a second cationic lipid layer obtained at the end of step 6 of Example 10.
Figure 5B:
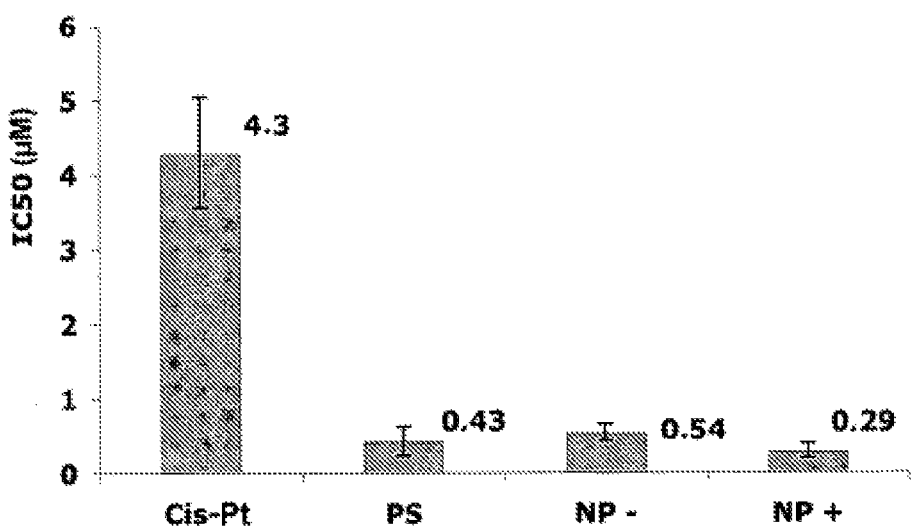

FIG. 5A relates to the cell line IGROV1 and FIG. 5B relates to the cell line SKOV3.

The results show that the NP+ nanoparticles containing cisplatin according to the invention are more effective than free cisplatin in the two cell lines, IGROV1 (cisplatin-sensitive) and SKOV3 (cisplatin-resistant).

On the line IGROV1, 50% cell death is obtained with 0.18 µM of nanoparticles containing NP+ cisplatin whereas 2.41 µM of free cisplatin must be used in order to obtain this result. On the line SKOV3, 50% cell death is obtained with 0.29 µM of NP+ nanoparticles containing cisplatin as against 4.3 µM of free cisplatin.

The nanoparticles containing cisplatin according to the invention (NP+) are respectively 13 and 14 times more effective than free cisplatin on the lines IGROV1 and SKOV3 respectively.

EXAMPLE 16

Demonstration of the Multiple-Compartment Structure of the Nanoparticles According to the Invention Formulations of nanoparticles were prepared with different labels, in order to study, on the one hand, the location of the label in the lipid layer, and, on the other hand, the state of the nanoparticles after their entry into the cells.

Lipiphilic fluorescent probes were inserted into the formulations as a label, on the one hand, and as a lipid compound mimicking a pro-drug (for example, a lipid conjugate analogue of an anticancer nucleoside such as 5-FU) on the other hand.

The following different formulations were produced:

Formulation A: diC16dT/DOPC 50/50

Formulation B: DOTAU/DOPC 50/50

Formulation C: diC16dT/DOPC/DOPE/fluorescein 49.25/49.25/0.5 ($\lambda$ ex=483 nm, $\lambda$ em=518 nm)

Formulation D: DOTAU/DOPC/DOPE/rhodamine 49.25/49.25/0.5 ($\lambda$ ex=550 nm, $\lambda$ em=590 nm)

The NP1, NP2 and NP3 nanoparticles according to the invention are thus prepared with different compositions, defined as follows:

| Nanoparticle | First layer | Second layer |
| --- | --- | --- |
| NP1 | Formulation C | Formulation B |
| NP2 | Formulation A | Formulation D |
| NP3 | Formulation C | Formulation D |

Figure 6:
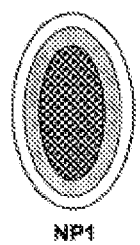
FIG. 6 shows schematic illustrations of nanoparticles according to the invention prepared with different compositions. In each of the nanoparticles, the white layer represents an unlabelled lipid layer, the grey layer represents a layer labelled with fluorescein, the black layer represents a layer labelled with rhodamine and the dotted centre represents incorporated cisplatin.
Figure 6:
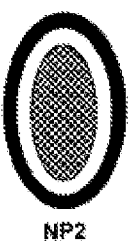
Figure 6:

The NP1, NP2 and NP3 nanoparticles are shown in FIG. 6. In each of the nanoparticles, the white layer represents an unlabelled lipid layer, the grey layer represents the layer labelled with fluorescein (formulation C), the black layer represents the layer labelled with rhodamine (formulation D) and the dotted centre represents incorporated cisplatin.

Figure 7:
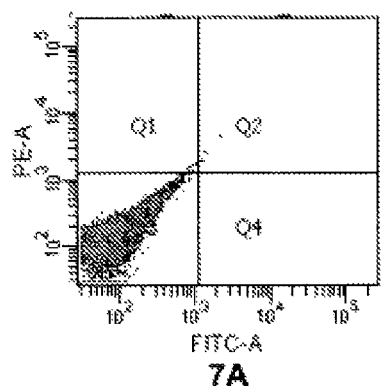
FIGS. 7A-7D show FACS (Fluorescence Activated Cell Sorting) measurements carried out on SKV03 cells which have been incubated:
in the absence of nanoparticles according to the invention as a control (FIG. 7A)
in the presence of nanoparticles in which the first layer is labelled (FIG. 7B),
in the presence of nanoparticles in which the second layer is labelled (FIG. 7C), and
in the presence of nanoparticles in which the two layers are labelled (FIG. 7D).
Figure 7:
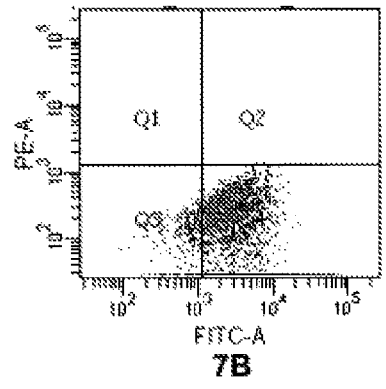
Figure 7:
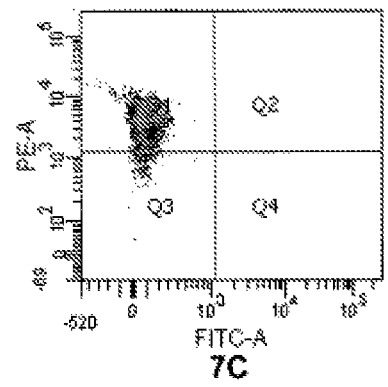
Figure 7:
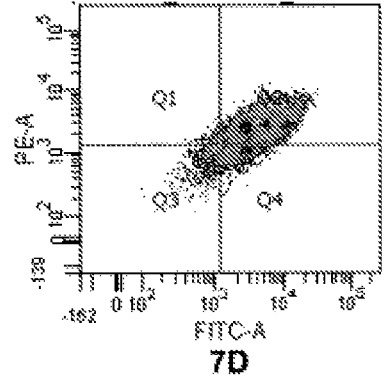

FACS (Fluorescence Activated Cell Sorting) measurements were carried out on SKV03 cells which had been incubated:
in the absence of nanoparticles according to the invention as a control (FIG. 7A)
in the presence of NP1 nanoparticles in which the first layer is labelled (FIG. 7B),
in the presence of NP2 nanoparticles in which the second layer is labelled (FIG. 7C), and
in the presence of NP3 nanoparticles in which the two layers are labelled (FIG. 7D).

The FACS data obtained show the presence of the two fluorescent labels (fluorescein, rhodamine) in the SKV03 cells after incubation in the presence of the NP3 nanoparticles bearing these labels. These results show, on the one hand, that the nanoparticles according to the invention have a multi-compartment structure, and, on the other hand, remain intact after internalization in the cells.

Fluorescence microscopy experiments have confirmed the results obtained by FACS. The images show that the labelled NP1, NP2 and NP3 nanoparticles are internalized intact in the SKVO3 cells

The invention claimed is:

1. A formulation in the form of nanoparticles with multiple compartments and constituted by a solid core containing a therapeutic agent, surrounded by at least two lipid layers of different polarity,
wherein at least one lipid layer is anionic and is constituted by at least one functional amphiphilic compound of formula (I)

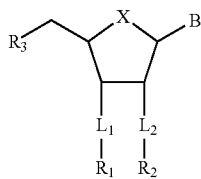

wherein
X represents an oxygen or sulphur atom or a methylene group,
B represents a purine or pyrimidine base, optionally substituted;
$L_1$ represents a phosphate group or a phosphonate group and $L_2$ represents hydrogen;
$R_1$ represents a diacyl chain in which each acyl chain is $C_2$-$C_{30}$, or a diacylglycerol in which each acyl chain is $C_2$-$C_{30}$;
$R_2$ does not exist;
$R_3$ represents a hydroxy, amino, phosphate or phosphonate group,
in order to obtain an anionic lipid layer,
and wherein at least one lipid layer, which has a polarity different from that of the previous one is cationic and is formed from compounds of formula (I) in which:
X represents an oxygen or sulphur atom or a methylene group;
B represents a purine or pyrimidine base;

$L_1$ and $L_2$, identical or different, represent an oxycarbonyl —O—C(O)— group, a thiocarbamate —O—C(S)—NH— group, a carbonate —O—C(O)—O— group, a carbamate —O—C(O)—NH— group, an oxygen atom;
$R_1$ and $R_2$, identical or different, represent a linear or branched $C_2$-$C_{30}$ hydrocarbon chain, saturated or partially unsaturated, optionally completely or partially fluorinated, unsubstituted or substituted on the carbon at the end of the chain by a fluorine atom or by a benzyl or naphthyl ester or ether;
$R_3$ represents a phosphonium, or $NR_4R_5R_6$ group in which $R_4$, $R_5$ and $R_6$, identical or different, represent a hydrogen atom or a linear or branched $C_1$-$C_5$ alkyl or a linear or branched $C_1$-$C_5$ hydroxyalkyl chain, or a heteroaryl group containing 1 to 4 nitrogen atoms, unsubstituted or substituted by a $C_2$-$C_{30}$ alkyl, or by a $(CH_2)_m$—O—$(CH_2)_p$—$R_9$ group in which m=1 to 6 and p=0 to 10 and $R_9$ represents a cyclic ketal group containing 5 to 7 carbon atoms, unsubstituted or substituted by at least one linear or branched $C_2$-$C_{30}$ alkyl or by a sterol radical,
in order to obtain a cationic lipid layer,
and each lipid layer has a polarity different from that of the previous one.

2. The formulation according to claim 1, wherein each lipid layer constitutes a compartment which can comprise a therapeutic agent identical to or different from that present in the core.

3. The formulation according to claim 1, wherein a co-lipid is present in at least one lipid layer.

4. The formulation according to claim 1, wherein the therapeutic agent is an anti-neoplastic agent.

5. The formulation according to claim 1, wherein the therapeutic agent is chosen from the platinum complexes or ruthenium capable of binding to platinum complexes, or also the inorganic complexes without platinum based on ruthenium II or III, titanium, gallium, cobalt, iron or gold.

6. The formulation according to claim 1, wherein the therapeutic agent is chosen from cisplatin, carboplatin, oxaliplatin, nedaplatin and lobaplatin.

7. The formulation according to claim 1, wherein, in formula (I), for both the at least one functional amphiphilic compound used for obtaining the at least one anionic lipid layer and the at least one functional amphiphilic compound used for obtaining the at least one cationic lipid layer, X represents oxygen.

8. The formulation according to claim 1, wherein, in formula (I), for both the at least one functional amphiphilic compound used for obtaining the at least one anionic lipid layer and the at least one functional amphiphilic compound used for obtaining the at least one cationic lipid layer, B represents thymine or adenine.

9. A method for preparing the formulation of claim 1, wherein the method
comprises the following steps:
a) preparing a mixture of at least one functional amphiphilic compound of formula (I) according to claim 1 and a therapeutic agent,
b) subjecting said mixture to repeated heating and freezing cycles, in order to obtain nanoparticles containing said therapeutic agent, and
c) recovering the nanoparticles containing said therapeutic agent obtained in step (b),
d) bringing said nanoparticles from step (c) into the presence of at least one functional amphiphilic compound of formula (I) according to claim 1 and, having a polarity different from that utilized in step a), and e) recovering the multi-compartment nanoparticles obtained from step (d).

10. The method according to claim 9, wherein a co-lipid is used during steps a) and/or d).

11. The method according to claim 9, further comprising adding a second therapeutic agent in step (d), wherein the second therapeutic agent is different from the therapeutic agent used in step a).

12. An agent for the transport or targeting of therapeutic agents comprising a formulation according to claim 1.

13. An agent for the intracellular delivery of therapeutic agents comprising a formulation according to claim 1.

14. A method of treating tumor diseases, which comprises administering to a subject in need thereof a formulation according to claim 1.

15. A pharmaceutical composition comprising a formulation according to claim 1 and a pharmaceutically acceptable vehicle.

16. The formulation of claim 1, wherein at least one lipid layer is formed from a compound of formula(I) in which
X is an oxygen atom,
$L_1$ is a phosphate group,
$L_2$ is hydrogen,
$R_1$ is a diacylglycerol group,
$R_2$ does not exist, and
$R_3$ is a hydroxyl group,
in order to obtain an anionic lipid layer.

17. The formulation of claim 1, wherein at least one cationic lipid layer is formed from a compound of formula(I) in which
X is an oxygen atom
$L_1$ and $L_2$ represent an oxycarbonyl group —(O)—C(O) group
$R_1$ and $R_2$, identical or different, represent a $C_6$-$C_{25}$ linear or branched hydrocarbon chain, saturated or partially unsaturated, and
$R_3$ represents a $NR_4R_5R_6$ group in which $R_4$, $R_5$ and $R_6$, identical or different, represent a hydrogen atom or a linear or branched $C_{1-5}$ alkyl,
in order to obtain a cationic lipid layer.

18. The formulation of claim 1, wherein, in formula (I), for both the at least one functional amphiphilic compound used for obtaining the at least one anionic lipid layer and the at least one functional amphiphilic compound used for obtaining the at least one cationic lipid layer, B is selected from the group of the purine and pyrimidine bases consisting of uracil, adenine, guanine, cytosine, thymine, and hypoxanthine.

19. The formulation of claim 1, wherein, in formula (I), for the at least one functional amphiphilic compound used for obtaining the at least one cationic lipid layer, $R_1$ and $R_2$, identical or different, represent a $C_8$-$C_{25}$, linear or branched hydrocarbon chain, saturated or partially unsaturated, optionally completely or partially fluorinated, unsubstituted or substituted on the carbon at the end of the chain by a fluorine atom or by a benzyl or naphthyl ester or ether.

* * * * *